United States Patent [19]
Kalinoski

[11] Patent Number: 5,193,553
[45] Date of Patent: Mar. 16, 1993

[54] MEDICAL DRAINAGE BAG CARRIER

[76] Inventor: Victoria Kalinoski, 1389 Bluebell Way, El Cajon, Calif. 92021

[21] Appl. No.: 688,308

[22] Filed: Apr. 22, 1991

[51] Int. Cl.$^5$ ............................................... A61B 5/00
[52] U.S. Cl. ........................... 128/767; 128/DIG. 24; 128/760
[58] Field of Search ............... 128/760, 761, 767, 768, 128/DIG. 24; 604/327–335

[56] References Cited

U.S. PATENT DOCUMENTS

| | | | |
|---|---|---|---|
| 3,186,409 | 6/1965 | Bartz | 604/330 |
| 4,122,851 | 10/1978 | Grosser | 604/330 |
| 4,511,358 | 4/1985 | Johnson, Jr. et al. | 604/327 |

OTHER PUBLICATIONS

Unitary Leg Bag—Marc Clark copyright 1986.

Primary Examiner—Randall L. Green
Assistant Examiner—R. Clarke

[57] ABSTRACT

The drainage bag carrier comprises a long, flattened envelope made of breathable fabric suspended from an elastic, releasable waistband. The envelope is attached to the waistband by hook and loop fasteners to allow adjustment of the length of the envelope hanging from the waistband. The drainage bag is inserted into the envelope through a slot in the outer side of the envelope, which faces outwardly from the wearer's leg. Fastening means are provided to support the drainage bag within the envelop—either medical rivets for disposable-type bags or hook and loop straps for reusable-type bags with side loops. On the inner side of the envelope, which is worn immediately adjacent to the wearer's leg, a support sleeve is placed around the leg to hold the envelope against the leg. The location of the support sleeve with respect to the drainage bag is adjustable along the length of the envelope. The envelope has pleats between the outer side and the inner side to permit expansion of the bag within the envelope. On the outer side of the envelope, just above the drainage bag, a tab is provided to hold the catheter tubing in place and to direct it downward to connect to the inlet of the drainage bag. A window is provided in the outer side of the envelope to view the contents of the drainage bag. An opening in the bottom of the envelope is provided for a drainage bag outlet.

20 Claims, 2 Drawing Sheets

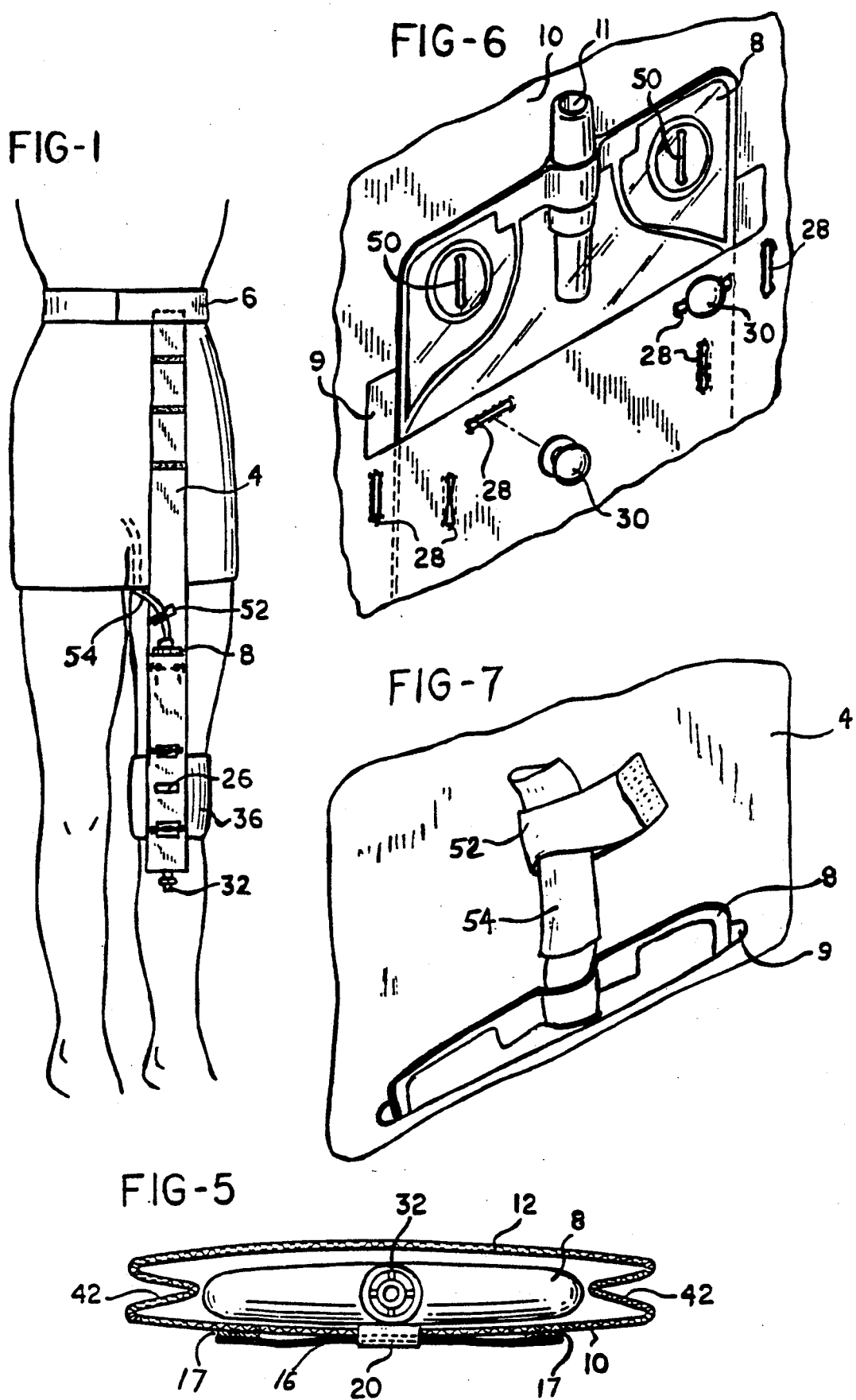

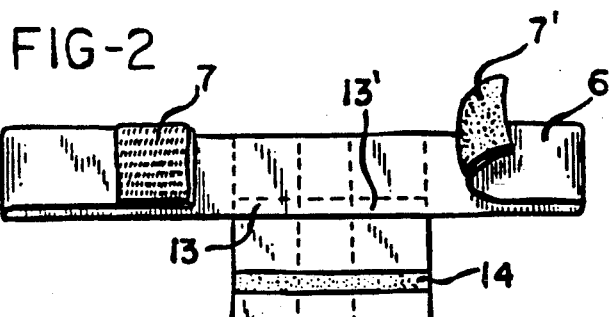
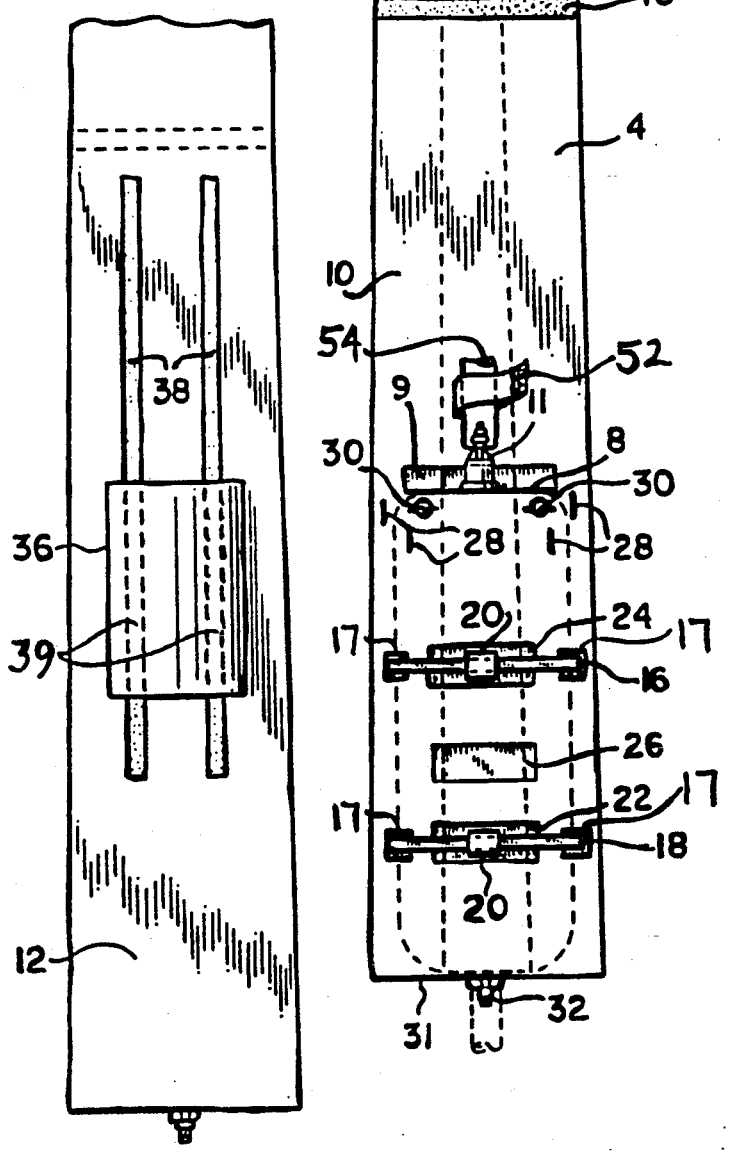
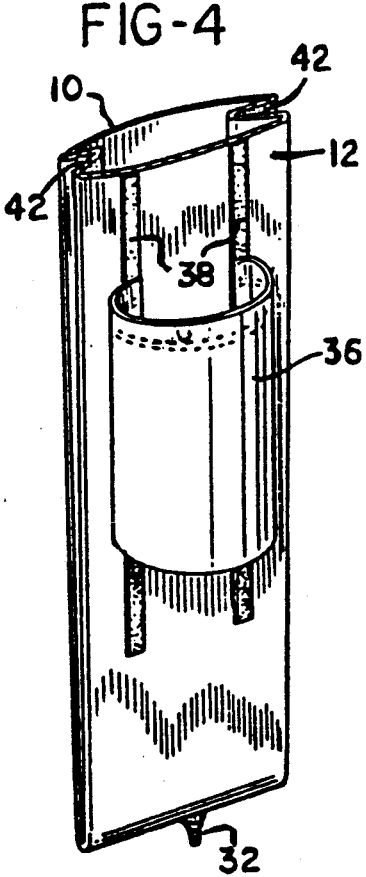

MEDICAL DRAINAGE BAG CARRIER

BACKGROUND OF THE INVENTION

This invention relates to carriers for receptacles used to receive discharge of body fluids, specifically to such carriers which are attached to the leg of the wearer.

Ambulatory patients who are required to have a catheter or tube in place for drainage of body fluid over an extended period of time are faced with a difficult and often uncomfortable situation of carrying a drainage bag wherever they go.

Early methods of permitting mobility included providing the drainage receptacle with a handle. This technique was still primarily limited to permit the patient to move from one treatment area to another and would not permit the patient to move readily in public without detection of the drainage system.

Many patents have been addressed to securing catheter tubing to some point of the body to prevent pulling out or shifting of the catheter (see, e.g., U.S. Pat. No. 3,878,849 of Moore, et al., No. 4,088,136 of Hasslinger, et al. and No. 4,569,348 of Hasslinger, et al.). The devices disclosed generally relate to straps which can be fastened around a limb. Similar straps are used for holding drainage bags on which loops or slotted openings are provided so that the straps may be threaded through them. For example, for a disposable leg bag, two sets of slotted openings are provided, one set each at the top and bottom. A strap runs through each set of slots and is then fastened around the patient's leg. Due to the weight of a filled bag, the straps must either be fastened very tightly, or must be located straddling the patient's knee so the knee can prevent the bag from slipping down. Either method can result in substantial discomfort for the user. In addition, the polymer or plastic of which the bags are made can result in additional discomfort when held directly against the skin so that it prevents the skin from breathing.

Devices for holding catheters, IV bags and drainage bags have been incorporated into wearing apparel such as vests, (see U.S. Pat. No. 4,087,864 of LaBove, et al., No. 4,504,267 of Parmalee, et al., and No. 4,578,062 of Schneider). None of these, however, address the concerns of a leg bag which is most often used with a urethral catheter.

U.S. Pat. No. 4,122,851 to Grossner (1978) describes a urine bag carrier that lacks the ability to be adjusted in length below the belt. This fixed length does not allow the carrier to be adapted to various body lengths and comfort zones. Grossner's design therefore prohibits the carrier from being attached to the leg since it resides mainly on the hip. With movement of the wearer, shifting and moving of the unrestrained bag could cause chaffing and irritation of the skin. Moreover, this same movement could cause pulling on the catheter which could produce irritating and/or bleeding in the wearer's urinary tract. This carrier does not provide for the use of reusable-type latex urinary bags, only the disposable type. With only a belt to support the increasing weight of a filling bag, this would only magnify the deficiencies of this design noted above.

Mark-Clark (publication) does not appear to have a means of adjusting the length of the carrier to adapt to differing body lengths of the wearer. The durability of a foam support belt backed with cotton flannel can be questioned. Mark-Clark shows a 2 inch wide leg strap at the base of the drainage bag for additional support. Experience has shown that a leg strap should be of substantially greater width to adequately support a filling urinary bag because with only the lower part of the bag supported, the bag will tend to slump and pull away from the wearer's leg as the bag fills. This design also requires the wearer to use drainage bags designed specifically for this system precluding the use of other disposable or reusable type bags.

The U.S. Pat. No. 3,186,409 to Bartz (1965) provides an adhesive tape to seal the drainage tube to the top of the drainage bag, but does not provide the stabilizing property of a tie-down strap to prevent pulling on the catheter.

U.S. Pat. No. 4,511,358 to Johnson, Jr. et al. (1985) fails to provide a method for securing a catheter to the drainage bag which would allow the tube to pull on the wearer with body movement. It provides no means of visually monitoring the fluid volume collected in the bag without removing the bag from the pouch. The narrow leg straps, if not tight enough, can slip or curl and roll up and down the leg with body movement. These straps, when worn for an extended time, can cause irritation. If the leg straps need to be tightened to support the additional weight of a filling drainage bag, they can become quite uncomfortable and restrict blood circulation.

It would be desirable to provide a carrier for drainage bags which can be worn comfortably and discretely, and which is adjustable for different sizes and comfort requirements of wearers. It is to such a device that the present invention is directed.

SUMMARY OF INVENTION

It is an advantage of the present invention to provide a carrier for medical drainage bags which will support the weight and expanded size of the full bag discretely without causing discomfort for the patient.

It is a further advantage of the present invention to provide a versatile carrier which can accommodate multiple forms of drainage bags.

It is still another advantage of the present invention to provide a support for maintaining a catheter in position without transferring stress which results as the weight of the drainage bag increases.

Another advantage is to provide such a support which can be adjusted in length for use by patients of a wide range of heights and sizes.

In an exemplary embodiment, the drainage bag carrier comprises a flattened envelope made of breathable fabric suspended from an elastic waistband and secured by a stretchable support sleeve. The envelope is attached to the waistband by hook and loop fastener strips to allow adjustment of the length of the envelope hanging from the waistband. The envelope is substantially closed at its lowermost end with a small opening at the center to provide an outlet for the drainage bag. The drainage bag is inserted into a slot in the outer side of the envelope, the slot being appropriately sized to permit insertion and removal of the bag. Once in position, the inlet of the bag will protrude through the slot allowing access to the catheter tubing. Fastening means are provided to support the bag within the envelope—either medical rivets for disposable-type bags, or hook and loop fastener straps for reusable-type bags with side loops. On the inner side of the envelope, which is worn immediately adjacent to the wearer's leg, a support sleeve is provided through which the leg is inserted to hold the envelope against the leg. The location of the support sleeve with respect to the drainage bag is adjustable by way of corresponding hook and loop fastener strips on the envelope and support sleeve. This allows the support sleeve to be moved up or down to the most comfortable location for the individual patient. The support sleeve has a length on the order of one-half the length of the bag to provide sufficient support to prevent the bag from slumping or pulling away from the leg as it fills. The envelope, which generally appears flat, has a pleat between the outer side and the inner side to permit expansion of the bag within the envelope.

On the outer side of the envelope, a tab is provided to hold the catheter in place and to direct it downward to connect to the inlet of the drainage bag. Except where the catheter exits the wearer's body, the catheter will lie against the envelope, thereby eliminating discomfort experienced by contact between the catheter and the skin.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which:

FIG. 1 is a side elevation of a patient wearing the carrier of the present invention;

FIG. 2 is a plan view of the outer side of the carrier;

FIG. 3 is a plan view of the inner side of the carrier;

FIG. 4 is a perspective view of the inner side:

FIG. 5 is a plan view looking up from the bottom of the carrier;

FIG. 6 is a perspective view illustrating insertion of a disposable bag; and

FIG. 7 is a perspective view illustrating the catheter support.

| REFERENCE NUMERALS LIST | | | |
|---|---|---|---|
| 2 | carrier | 18 | bag support strap |
| 4 | envelope | 20 | bag support loop |
| 6 | waistband | 22 | lower window |
| 7 | waistband fastener | 24 | upper window |
| 7' | waistband fastener | 26 | middle window |
| 8 | drainage bag | 28 | button holes |
| 9 | slot | 30 | medical rivets |
| 10 | outer side | 31 | bottom |
| 11 | inlet nipple | 32 | outlet nipple |
| 12 | inner side | 36 | support sleeve |
| 13 | carrier fastener | 38 | sleeve anchorage |
| 13' | carrier anchorage | 39 | sleeve fastener |
| 14 | carrier fastener | 42 | pleat |
| 15 | carrier fastener | 50 | slits |
| 16 | bag support strap | 52 | catheter strap |
| 17 | strap anchor | 54 | catheter |

DETAILED DESCRIPTION OF THE PREFERRED EMBODIMENTS

As illustrated in FIG. 1 the drainage bag carrier 2 comprises a waistband from which a long, flat, fabric envelope 4 is suspended and secured to the leg of a wearer by a support sleeve 36; a drainage bag 8 is supported within the envelope 4.

As illustrated in FIG. 2, the outer side 10, a slot 9 and a plurality of windows 22, 24 and 26 are provided. Slot 9 provides means for inserting and removing drainage bag 8. Inlet nipple 11 protrudes through slot 9 to permit access to a catheter 54. The bottom 31 of envelope 4 is sewn closed with the exception of an opening through which an outlet nipple 32 may protrude for access to drain fluid from the drainage bag 8. The lower shoulder of drainage bag 8 is supported by the bottom 31.

The drainage bag carrier 2 is designed to accommodate both reusable and disposable drainage bags.

The drainage bag 8 illustrated in FIGS. 2 and 5 is of the reusable type. Two or more bag support loops 20 are formed on the side wall of drainage bag 8. Windows 22 and 24 are located such that they will coincide with the locations of bag support loops 20 so that two of the bag support loops 20 will protrude through the windows 22 and 24. Bag support straps 16 and 18 are located such that they span the lengths of windows 24 and 22 respectively. Each bag support strap 16 and 18, composed of hook material, is threaded through its respective bag support loop 20 and each end is attached to the envelope 4 by strap anchors 17 composed of small pieces of loop material which are sewn onto outer side 10.

The drainage bag 8 illustrated in FIG. 6 is of the disposable type, which does not have bag support loops. For support of this type bag, buttonholes 28 are located just below slot 9 so that medical rivets 30 can be inserted and held firmly therein. The locations of buttonholes 28 correspond to slits 50 in the top of drainage bag 8. The rivets 30 are inserted into slits 50 to support the drainage bag 8 within the envelope 4. Several sets of buttonholes are provided to accommodate different spacings and configurations of slits in different drainage bags.

Window 26 is located approximately halfway between windows 22 and 24 to provide visual access to the fluid level in the drainage bag 8.

As illustrated in FIG. 7, a catheter strap 52 is located a short distance above slot 9. The catheter strap 52 is a short length of hook and loop fastener material with one end stitched to the outer side 10 in such a way that the loose end is looped over the catheter 54 and folded back upon and fastened to the fixed end.

As illustrated in FIG. 2, at the top of envelope 4, a plurality of parallel carrier fasteners 13, 14, and 15 are sewn to the outer side 10. These carrier fasteners are preferably composed of hook material so that the stiffer hooks face away from the wearer's body. A corresponding carrier anchorage 13', composed of loop material, is attached to the inside of waistband 6. The length of the envelope 4 is adjusted to fit the wearer's height by attaching carrier anchorage 13' to either of carrier fasteners 13, 14 or 15.

Waistband 6 can be either a wide band of elastic or other stretchable material sewn into a circle, or can be openable with a waistband fastener 7 and 7' composed of hook and loop fastener material, or other fastener to permit adjustment of the waist size.

Illustrated in FIGS. 3 and 4 is the inner side 12 of envelope 4 which is held immediately adjacent to the wearer's leg by support sleeve 36. Along the inner side 12 of envelope 4, a pair of long, parallel sleeve anchorages 38, composed of loop material, are sewn vertically. Sleeve fasteners 39, composed of hook material, are sewn to the vertical ends of the fabric of which support sleeve 3 is made. Support sleeve 36 encircles the wearer's leg and is secured by folding the sleeve fasteners 39 on the support sleeve 86 back onto their respective sleeve anchorage 38 on the inner side 12 of the envelope 4.

In FIGS. 4 and 5, pleats 42 are shown at the sides of the envelope 4, between outer side 10 and inner side 12. Pleats 42 are sewn through at both the top and bottom of envelope 4.

The fabric of which the envelope 4 is made is preferably cotton, cotton blend or a similar breathable and durable fabric. It is also desirable that the fabric be of a weave and texture to avoid chafing the skin of the wearer.

The hook and loop fasteners have been specifically described as to the preferred location of the loop portion and the hook portion. The locations were selected to optimize comfort for the wearer by avoiding contact between the hook portion and the wearer's skin. The relative locations of the loop and hook portions can be reversed without affecting the utility of the invention.

While the preferred embodiment has been described as using hook and loop fasteners, it is foreseeable that other fastening means such as snaps, buttons, hooks and eyes, etc., may be substituted and fall within the scope of the invention.

From the description above, a number of advantages of this drainage bag carrier are evident:

(a) The carrier is suspended from a wide, adjustable and releasable elastic waistband.

(b) The carrier envelope is made of a breathable fabric that is easily cleaned or laundered and comfortable to wear.

(c) The carrier length hanging from the waistband is easily adjustable to better suit a wide range of wearers. Thereby the drainage bag supported within the envelope can be positioned along the most comfortable and convenient location of the wearer's leg.

(d) The carrier can accommodate either disposable or reusable type drainage bags. A fastening means suitable to each type of drainage bag is provided.

(e) The envelope has a viewing window to monitor the accumulating volume of body fluid collected in the drainage bag.

(f) The envelope is constructed in such a way that the top of the drainage bag, inserted through the slot protrudes sufficiently for access to the inlet nipple, and the outlet nipple can be accessed through the bottom of the envelope.

(g) The carrier envelope construction will adequately support the weight and contain the expanding size of the drainage bag as it fills.

(h) A means of securing the catheter to the carrier is provided preventing the catheter from disconnecting from the input nipple or irritating the wearer with body movement.

(i) A wide, detachable, support sleeve encircling the wearer's leg and attached to the inner side of the envelope, adequately supports the drainage bag and prevents it from slumping and pulling away from the leg as it fills. Moreover, together with the adjustable length carrier, the drainage bag supported within the envelope can be placed in the most comfortable, convenient and supportable location on the wearer's leg. This combination sufficiently immobilizes the drainage bag within the carrier envelope and allows the wearer complete freedom of movement and confidence without discomfort.

It will be evident that there are additional embodiments which are not illustrated above but which are clearly within the scope and spirit of the present invention. The above description and drawings are therefore intended to be exemplary only and the scope of the invention is to limited soley by the appended claims.

I claim:

1. A carrier attached to a wearer for supporting drainage bag to collect body fluids from a catheter comprising:
    a flattened fabric envelope having a top, a bottom, and two planar sides, a flat inner side for contacting said wearer's leg and a second outer side for facing outwardly from said wearer's leg, said bottom being substantially closed, said envelope being of a size to receive and retain therein a drainage bag;
    a slot of appropriate size and shape in said outer side of said envelope through which said drainage bag can be inserted and removed;
    a fastening means for supporting said drainage bag vertically within said envelope;
    a releasable strap slightly above said slot for securing said catheter to said outer side of said envelope;
    a releasable waistband from which said top of said envelope is suspended by a plurality attachment means;
    a substantially wide support sleeve releasably attached to said inner side of said envelope, said support sleeve encircling said wearer's leg to hold said inner side of said envelope containing said drainage bag firmly against said wearer's leg.

2. The carrier of claim 1 wherein said slot is located in such a way that an inlet nipple located on the top of said drainage bag protrudes above the opening of said slot sufficiently to permit attaching said catheter through which said body fluids is drained and collected.

3. The carrier of claim 1 wherein said bottom of said envelope has a centrally located small opening through which an outlet nipple of said drainage bag may be accessed for the purpose of draining said body fluid collected.

4. The carrier of claim 1 wherein said envelope has a pleat on opposite sides between said outer side and said inner side whereby said envelope may expand as said drainage bag fills.

5. The carrier of claim 1 wherein said outer side of said envelope has a horizontally rectangular middle window, therein disposed at a location relative to said drainage bag fasteners within said said envelope such that the level of said body fluid within said drainage bag can be viewed.

6. The carrier of claim 1 wherein said fastening means adaptable to suport a variety of said drainage bags.

7. The carrier of claim 6 wherein said fastening means for a reusable type of said drainage bags comprises medical rivets that secure vertical slits found on the top corners of said reusable type drainage bags to a plurality of buttonholes located just below said slot on said outer side of said envelope, whereby said drainage bag can be supported within said envelope.

8. The carrier of claim 7 wherein several sets of said butonholes are provided to accommodate different spacings and configurations of said slits in said reusable type drainage bags.

9. The carrier of claim 6 wherein said fastening means for a disposable type of said drainage bags comprises a upper and a lower bag support strap that pass through corresponding support loops found on the outside wall of said disposable type drainage bag, said bag support loops protrude through corresponding horizontally rectangular upper and lower windows on said outer side of said envelope, said support straps span the width of said upper and lower windows.

10. The carrier of claim 9 wherein said bag support straps are comprised of hook material and are fastened to a strap anchor comprised of a small piece of loop material fixed onto said outer side of said envelope near both extreme ends of said upper and lower windows, whereby said drainage bag can be supported within said envelope.

11. The carrier of claim 1 wherein said catheter strap comprises a short length of hook and loop material, one end of said catheter strap is fixed onto said envelope in such a way that the free end can looped around and over said catheter and folded back upon the fixed end of said strap whereby said catheter is firmly secured to said envelope.

12. The carrier of claim 1 wherein said plurality of attachment means comprises at least three carrier fasteners spaced at regular intervals from said top of said envelope.

13. The carrier of claim 12 wherein each of said carrier fasteners comprises a strip of hook material fixed horizontally across the entire width of said outer side of said top of said envelope.

14. The carrier of claim 1 wherein said waistband has fixed upon the inside lower edge of said waistband a carrier anchorage means comprising a strip of loop material of at least the width of said top of said envelope.

15. The carrier of claim 1 wherein said carrier anchorage upon said waistband is mated with one of said carrier fasteners upon said top of said envelope, whereby said envelope is suspended from said waistband at a convenient and comfortable location along said wearer's leg.

16. The carrier of claim 1 wherein said waistband is made of a wide elastic or otherwise stretchable material of sufficient length to encircle said wearer's waist.

17. The carrier of claim 1 wherein one free end of said waistband has fixed upon its outside a waistband fastener means comprising a square of hook material of approximately the same dimension as the width of said waistband, the opposite free end of said waistband has fixed upon its inside a comparable square of loop material, whereby said waistband can be securely and comfortably fastened about said wearer's waist.

18. The carrier of claim 1 wherein along a substantial length of said inner side of said envelope a pair of parallel sleeve anchorage means are fixed, said sleeve anchorage comprising a long strip of loop material.

19. The carrier of claim 1 wherein said support sleeve comprises a piece of soft, woven, stretchable, breathable material at least eight inches in length and of substantial width to adequately encircle said wearer's leg, along the entire length of each free end of said support sleeve a sleeve fastener means is fixed, said sleeve fastener comprises a long strip of hook material.

20. The carrier of claim 1 wherein said support sleeve is located at a position along said wearer's leg relative to the location of said drainage bag supported within said envelope, said support sleeve encircling said wearer's leg with said sleeve fastener means of said support sleeve folded back and mated with said sleeve anchorage means on said inner side of said envelope, whereby said envelope extends along said wearer's leg for a desired length, said length being adjusted by attaching said envelope by one of said plurality of attachment means to said waistband, thereby enabling the weight of said drainage bag within said envelope to be borne by said wearer's waistband and substantially by said support sleeve encircling said wearer's leg and the position of said drainage bag within said envelope maintained in a secure and comfortable manner regardless of the position of said wearer.

* * * * *